United States Patent
Brohan et al.

(10) Patent No.: US 7,758,519 B2
(45) Date of Patent: Jul. 20, 2010

(54) SYSTEMS FOR AND METHODS OF ASSESSING LOWER URINARY TRACT FUNCTION VIA SOUND ANALYSIS

(75) Inventors: John Brohan, Montreal (CA); Peter Zvara, Stowe, VT (US); Katarina Zvarova, Stowe, VT (US)

(73) Assignee: University of Vermont and State Agriculture College, Burlington, VT (US)

( * ) Notice: Subject to any disclaimer, the term of this patent is extended or adjusted under 35 U.S.C. 154(b) by 0 days.

(21) Appl. No.: 12/123,145

(22) Filed: May 19, 2008

(65) Prior Publication Data

US 2008/0275366 A1 Nov. 6, 2008

Related U.S. Application Data

(63) Continuation-in-part of application No. 11/530,314, filed on Sep. 8, 2006.

(51) Int. Cl.
- *A61B 5/00* (2006.01)
- *B65D 81/00* (2006.01)
- *A61B 5/103* (2006.01)
- *A61B 5/117* (2006.01)

(52) U.S. Cl. ...................... 600/584; 600/587
(58) Field of Classification Search .......... 600/561, 600/573, 584; 702/104
See application file for complete search history.

(56) References Cited

U.S. PATENT DOCUMENTS 3,363,619 A * 1/1968 Keitzer ................ 600/584
3,561,427 A   2/1971 Profy
4,063,548 A  12/1977 Klatt et al.
4,099,412 A   7/1978 Nehrbass (Continued)

FOREIGN PATENT DOCUMENTS

DE          3541649         4/1987

(Continued)

OTHER PUBLICATIONS

"Assessment of an Electronic Daily Diary In Patients With Overactive Bladder," by P. Quinn, J. Goka and H. Richardson. Pfizer, Sandwich, Kent, UK. 2003 BJU International, 91, pp. 647-652.

(Continued)

*Primary Examiner*—Max Hindenburg
*Assistant Examiner*—Adam J Eiseman
(74) *Attorney, Agent, or Firm*—Downs Rachlin Martin PLLC

(57) ABSTRACT

Systems for and methods of assessing lower urinary tract function from urinary flow data via sound analysis and user-provided information regarding the lower urinary tract symptoms (LUTS) of frequency, urgency and urge incontinence. Embodiments of the LUTS assessment systems include a computer and a telephone or a digital recording mechanism to capture the sound of one or more urination events, which are stored as audio files in a database. The LUTS assessment systems may include sound analysis software for analyzing the strength and duration of each urination event and may include a web-based software application for viewing the results via the Internet or other network. The database stores information from multiple urination events, and combined with information regarding the lower urinary tract symptoms, serves as an objective tool to assess bladder function and monitor progression of disease or therapy effectiveness.

23 Claims, 10 Drawing Sheets

U.S. PATENT DOCUMENTS

| | | | |
|---|---|---|---|
| 4,343,316 | A | 8/1982 | Jespersen |
| 4,448,207 | A | 5/1984 | Parrish |
| 4,554,687 | A | 11/1985 | Carter et al. |
| 4,589,280 | A | 5/1986 | Carter |
| 4,658,834 | A | 4/1987 | Blankenship et al. |
| 4,683,748 | A | 8/1987 | Carter |
| 4,732,160 | A | 3/1988 | Ask et al. |
| 5,062,304 | A | 11/1991 | Van Buskirk et al. |
| 5,078,012 | A | 1/1992 | Ding et al. |
| 5,176,148 | A | 1/1993 | Wiest et al. |
| 5,331,548 | A | 7/1994 | Rollema et al. |
| 5,377,101 | A | 12/1994 | Rollema |
| 5,410,471 | A | 4/1995 | Alyfuku et al. |
| 5,495,854 | A | 3/1996 | Currie |
| 5,807,278 | A | 9/1998 | McRae |
| 5,823,972 | A | 10/1998 | McRae |
| 5,891,051 | A | 4/1999 | Han et al. |
| 6,506,169 | B2 | 1/2003 | Griffiths |
| 6,904,809 | B1 | 6/2005 | Aundal |
| 6,916,283 | B2 | 7/2005 | Tracey et al. |
| 6,931,943 | B1 | 8/2005 | Aundal |
| 7,194,369 | B2 * | 3/2007 | Lundstedt et al. ........... 702/104 |
| 2003/0097039 | A1 | 5/2003 | Besson et al. |
| 2004/0260163 | A1 | 12/2004 | Kron et al. |
| 2004/0260540 | A1 | 12/2004 | Zhang |
| 2006/0020225 | A1 * | 1/2006 | Gerber et al. ............... 600/561 |
| 2008/0082022 | A1 | 4/2008 | Brohan et al. |

FOREIGN PATENT DOCUMENTS

| | | |
|---|---|---|
| GB | 1219231 | 1/1971 |
| WO | WO2004084089 | 9/2004 |
| WO | WO2007128539 | 11/2007 |
| WO | 2008030692 | 3/2008 |
| WO | 2009143113 | 11/2009 |

OTHER PUBLICATIONS

"A review of randomized controlled trials comparing the effectiveness of hand held computers with paper methods for data collection," by Shannon J. Lane, Nancy M. Heddle, Emmy Arnold and Irwin Walker. BMC Medical Informatics and Decision Making 2006, 6:23, 10 pages.

"The Voiding Audiograph: A New Voiding Test," by Walter A. Keitzer and Gene C. Huffman, The Journal of Urology, vol. 96, pp. 404-411, 1996.

"Urophonographic Studies of Benign Prostatic Hypertrophy," by Kenkicki Koiso, Ryosuke Nemoto and Mikinobu Ohtani, The Journal of Urology, vol. 145, pp. 1071-1077, May 1991.

Related pending International Application No. PCT/US2007/076108 filed Aug. 16, 2007.

Related pending International Application No. PCT/US2009/044464 filed May 19, 2009.

Related pending U.S. Appl. No. 11/530,314 filed Sep. 8, 2006.

International Search Report and Written Opinion dated Mar. 6, 2008 in related pending International Application No. PCT/US2007/076108 filed Aug. 16, 2007.

First Office Action dated Nov. 26, 2008 in related pending U.S. Appl. No. 11/530,314.

Response to first Office Action dated Feb. 19, 2009 in related pending U.S. Appl. No. 11/530,314.

Final Office Action dated Apr. 2, 2009 in related pending U.S. Appl. No. 11/530,314.

Response to Final Office Action dated Jul. 2, 2009 in related pending U.S. Appl. No. 11/530,314.

Advisory Action dated Jul. 16, 2009 in related pending U.S. Appl. No. 11/530,314.

RCE dated Aug. 26, 2009 in related pending U.S. Appl. No. 11/530,314.

Article 19 Amendment filed Sep. 29, 2009 in connection with related International Application No. PCT/US2009/044464, Inventors Xindong Wu and Xingquan Zhu.

First Office Action After RCE dated Sep. 11, 2009 in connection with related U.S. Appl. No. 11/530,314.

Response to Office Action dated Dec. 11, 2009 in connection with related U.S. Appl. No. 11/530,314.

Office Action dated Feb. 19, 2010 in connection with related U.S. Appl. No. 11/530,314.

* cited by examiner

SYSTEMS FOR AND METHODS OF ASSESSING LOWER URINARY TRACT FUNCTION VIA SOUND ANALYSIS

RELATED APPLICATION DATA

This application is a continuation-in-part and claims the benefit of priority of U.S. Nonprovisional patent application Ser. No. 11/530,314, filed Sep. 8, 2006, titled "Systems For and Methods of Assessing Urinary Flow Rate Via Sound Analysis," which is incorporated herein by reference in its entirety.

FIELD OF INVENTION

The present invention generally relates to the field of urinary flow analysis. In particular, the present invention is directed to systems for and methods of assessing function of the lower urinary tract via sound analysis of urination and lower urinary tract symptom information provided by a user.

BACKGROUND

The widely used measurement of a urinary flow rate is the simplest investigation in the assessment of voiding dysfunction. The urinary flow rate provides important and useful information about whether a problem exists in a patient's lower urinary tract. Additionally, the measurement of urinary flow rate may indicate the degree and possible etiology of an ongoing bladder pathology.

A uroflowmeter is a well-known device for measuring the rate of urine flow. Uroflowmeters that are commonly used today operate using one of three well-known methods: (1) a rotating disk method, (2) an electronic dipstick method, or (3) a gravimetric method. With the rotating disk method, voided fluid is directed onto a rotating disk and the amount landing on the disk produces a proportionate increase in its inertia. The power required to keep the disk rotating at a constant rate is measured, allowing calculation of the flow rate of fluid. In the electronic dipstick method, a dipstick is mounted in a collecting chamber and as urine accumulates the electrical capacitance of the dipstick changes, allowing calculation of the rate of fluid accumulation and hence the flow rate. With the gravimetric method, the weight of collected fluid or the hydrostatic pressure at the base of collecting cylinder is measured.

Standard uroflowmetry is performed at specified procedure areas by having a person urinate into a special funnel that is connected to a measuring instrument. Normally, standard uroflowmetry is performed on an outpatient basis at urology clinics or as part of patient stay in the hospital. Commercially available uroflowmeters require maintenance, are large in size and the procedure itself takes a lot of clinic time. Importantly, the voiding process is somewhat unnatural and the patient's privacy and comfort are limited. Furthermore, the use of uroflowmeters in hospitals and doctor's offices poses a risk to medical personnel of contacting urine excrements. Additionally, collecting data using today's commercially available portable uroflowmeters is still impractical because they are available only to a limited number of patients producing only limited number of measurements.

Hand-held computers and pen-and-pencil voiding diaries have been used to collect information regarding urination events including volume, frequency and urgency of urination. The sound of urination is apparently not collected with such computers, and the data are not recorded automatically, but rather are elicited via answers to specific questions.

The sound of urine flow through the urethra has been recorded in electronic format and analyzed to develop a graphic depiction of characteristics of the urination in patients with urethral narrowing due to stricture. It is believed that no prediction of lower urinary tract function has been made using such sound information, alone or with data regarding the urgency of urination.

For these reasons, a need exists for improved systems for and methods of assessing lower urinary tract function and symptoms associated with dysfunction in a manner that is convenient and easy to use in a non-stressful and risk-free environment by persons with limited training.

SUMMARY OF THE DISCLOSURE

In one implementation, the present disclosure is directed to a method of assessing lower urinary tract function of a person. The method includes capturing the sound of a person's micturition with a sound-capture device; providing information with respect to one or more lower urinary tract symptoms associated with the micturition using the sound-capture device; and analyzing the sound of micturition to determine at least one of the following attributes of the micturition: strength and duration.

In another implementation, the present disclosure is directed to a method of assessing lower urinary tract function of a person. The method includes transferring the sound of a person's micturition from a first location to a second location remote from the first location, wherein the transferring occurs substantially simultaneously with the micturition via a telecommunications network; providing information with respect to one or more lower urinary tract symptoms associated with the micturition from the first location to the second location via the telecommunications network immediately before or after the micturition; and analyzing the sound of micturition to determine at least one attribute of the micturition.

In still another implementation, the present disclosure is directed to a system for assessing lower urinary tract function of a person using urinary flow data and lower urinary tract symptom data from the person. The system includes a database in which may be stored (i) an audio file including information representing the sound of urination of a person and (ii) lower urinary tract symptom data for the person; and a device for obtaining and, when connected to a telecommunications network, providing to the database via the telecommunications network, both the sound of urination of a person and lower urinary tract symptom data for the person.

In yet another implementation, the present disclosure is directed to a computer-implemented system for assessing lower urinary tract function of a person using urinary flow data and lower urinary tract symptom data from the person. The system includes a database in which may be stored (i) an audio file including information representing the sound of urination of a person and (ii) lower urinary tract symptom data for the person; and a software program in communication with the database that analyzes the sound of urination to define at least one of the following: strength and duration.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

DETAILED DESCRIPTION

The present disclosure is directed to a system and method for determining lower urinary tract function in a manner more convenient than that typically available with known systems. In one embodiment, the sounds of urination in a receptacle such as a toilet are captured using a microphone or other device and are converted to an electronic format, e.g., a digital audio file. Sound analysis software is used to evaluate the information in the audio file and, together with lower urinary tract symptoms ("LUTS") information with respect to the person urinating, provides a collection of information that may be used to diagnose LUTS and bladder overactivity. This information may also be used in connection with diagnosing diseases responsible for LUTS and bladder overactivity, and for other purposes. In another embodiment, a telephone is used to capture the sounds of urination which are communicated via a telephone system to management software and then to sound analysis software where analysis of urination sounds is performed. Either embodiment may be implemented via a website system, and alternatively, the audio file containing urination sound information may be sent by email or other means to the website system.

Figure 1:
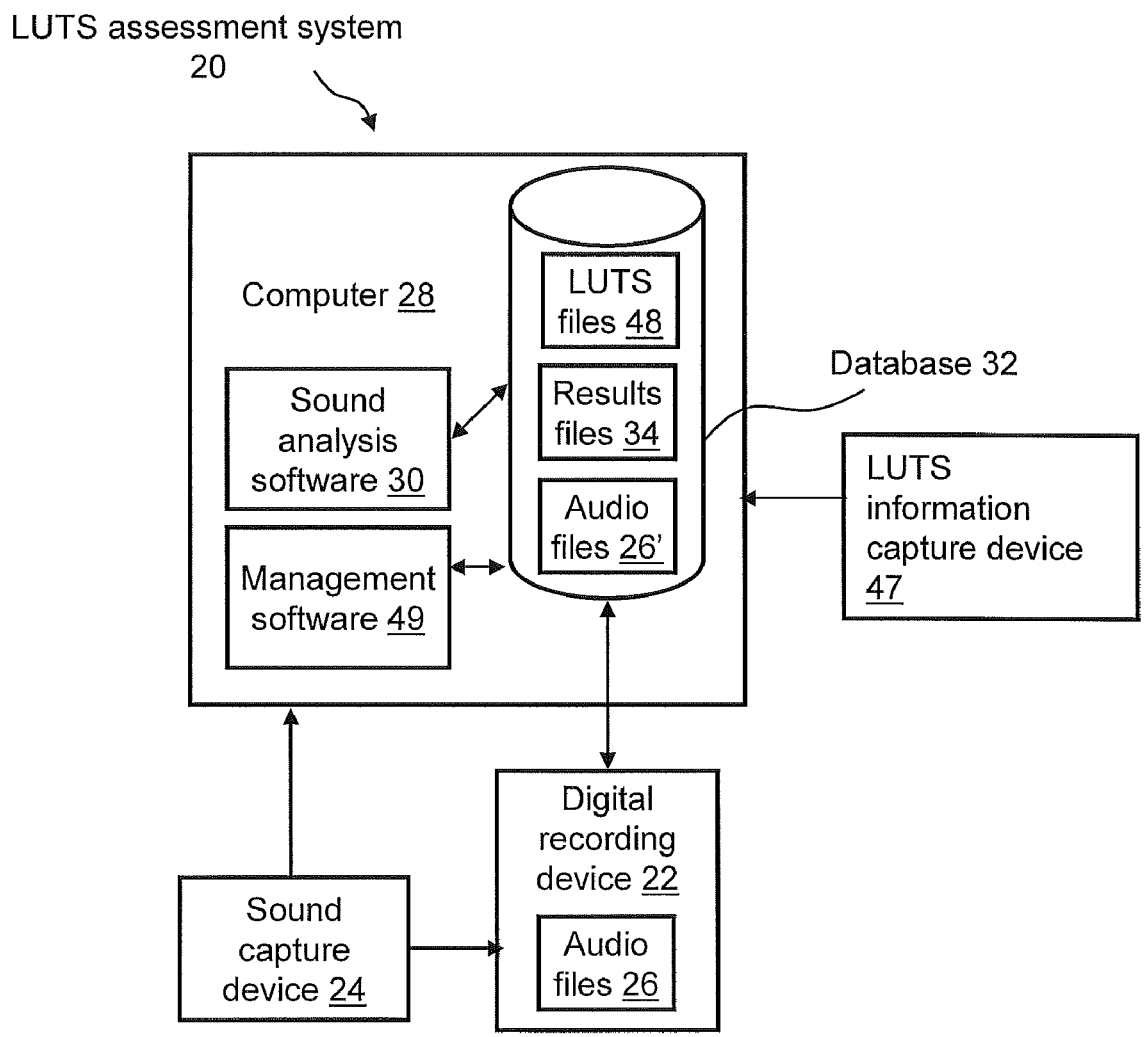
FIG. 1 illustrates a functional block diagram of a LUTS assessment system, in accordance with a first embodiment of the disclosure.

FIG. 1 illustrates a functional block diagram of a LUTS assessment system 20, in accordance with a first embodiment of the disclosure. LUTS assessment system 20 provides mechanisms for measuring urinary flow by digitally capturing the sound of a patient urinating into a receptacle such as a toilet and, subsequently, performing an analysis thereof. LUTS assessment system 20 may be implemented as a unitary assembly or may include different elements that together form the system.

LUTS assessment system 20 may, in one implementation, include a digital recording device 22 and a sound-capture device 24 (i.e., a microphone or any other sound-capture device). Additionally, a set of files such as audio files 26 are generated by, and stored in digital recording device 22. Typically, although not necessarily, audio files 26 are digital files. LUTS assessment system 20 further includes a computer 28 that comprises sound analysis software 30 and a database 32 upon which is stored a set of audio files 26' (typically but not necessarily digital files) and a set of results files 34. In some cases, sound-capture device 24 may be connected directly to, or be an integral part of, computer 28, with the result that the audio file is recorded and stored on the computer. In the latter case, computer 28 includes sound-capture and recording capabilities. In other implementations in which digital recording device 22 is not used, sound-capture device 24 may be connected with computer 28 via a network, e.g., a telecommunications network.

Digital recording device 22 may be any commercially available portable sound recorder capable of capturing an audio input signal of sound-capture device 24 and storing a representation thereof (i.e., any one of audio files 26) in any suitable audio file format, such as WAV format or MP3 format. Digital recording device 22 has a recording frequency in the range of, for example, but not limited to, 8000 to 44100 hertz (Hz). Additionally, digital recording device 22 may have an input/output port, such as, but not limited to, a universal serial bus (USB) port or firewire port, for transferring audio files 26 to an external computer, such as to computer 28. In other embodiments, digital recording device 22 may include a removable memory card (not shown) or other removable storage medium for transferring audio files 26 to an external computer. In yet other embodiments, digital recording device 22 may be integrated with computer 28. An example digital recording device 22 is the Sony ICB300 Digital Voice Recorder available from Sony Corporation, Tokyo, Japan. Sound-capture device 24 may be a conventional microphone that is built into digital recording device 22. Alternatively, sound-capture device 24 may, for example, be an external microphone that is in either wired or wireless communication with digital recording device 22. In the case of an external microphone, the use of a water resistant and/or floating microphone may be beneficial.

In the context of LUTS assessment system 20, the combination of digital recording device 22 and sound-capture device 24 is one example of a mechanism for capturing the sound of a patient urinating into a receptacle such as a toilet, i.e., for capturing the sound of the urine stream hitting the water or side of the receptacle in a water-less system. Each audio file 26 of digital recording device 22 is typically associated with a single urination event, although in some cases it may be desirable to use a single audio file 26 for multiple urination events.

Computer 28 may be any computer or computing resource, such as a handheld, laptop, desktop, or networked computer, that utilizes any suitable operating system, such as Microsoft Windows® 2000, Windows XP, Unix, Linux or Macintosh, that is capable of executing commercially available software applications or custom software applications, such as sound analysis software 30. Computer 28 typically includes a display for displaying the results of analysis of the sounds of urination and selected LUTS information, as described more below. When LUTS assessment system 20 is implemented as a unitary assembly, computer 28 may be a component of such assembly.

Database 32 may be created and maintained by any suitable database software, such as Oracle database software available from Oracle Corporation (Redwood Shores, Calif.) or MySQL, that stores relationships between patients and their associated audio files 26' and results files 34. Audio files 26' are audio files 26 of digital recording device 22 that have been transferred to database 32 of computer 28. Each audio file 26' will typically, although not necessarily, be associated with a particular patient. Results files 34 are data files that contain the results of the digital analysis of respective audio files 26'. The analysis is performed by sound analysis software 30, as described below.

Sound analysis software 30 is a software application that performs an analysis upon audio files 26', which, in the context of LUTS assessment system 20, may contain a digital representation of the sound of a patient expelling urine into a suitable receptacle, such as a toilet, i.e., a digital representation of the sound of a urine stream. In one example, the audio file may be a digital representation of the sound of urine striking the water in the toilet or the sides of the toilet where water is not maintained in the toilet bowl, or any other sound associated with urination. More specifically, sound analysis software 30 may provide a visual/graphic analysis of a urination event and/or a set of numerical values that correspond to the strength and duration of the urination event. The present LUTS assessment system encompasses the use of any software for achieving the functions of software 30 described herein, as those of ordinary skill in the art will appreciate. The operations that are performed by sound analysis software 30 may include, but are not limited to, the following:

(a) reading in the raw data of a selected audio file 26'. In doing so, the selected audio file 26' is converted into an array of amplitude readings at, for example, 8,000 data points per second;

(b) generating a plot of audio signal amplitude vs. time. An example of such a raw data plot 40 appears in FIG. 2A. The audio signal amplitude represented in such a plot may be shown simply as the relative magnitude of the sound (i.e., no units), or may be shown as the fraction of the full possible amplitude of the sound signal, voltage, or any unit of sound volume; or a mathematical formula may be used to estimate the peak and average flow in mL/sec.;

(c) generating a plot of smoothed data for the purpose of presenting an outline of the flow. For example, an envelope is calculated from the maximum positive amplitude per 100 data points. An example of such a smoothed data plot 42 appears in FIG. 2B;

(d) referring to the smoothed data plot of the above-mentioned item (b), removing points that are less than a user-selected minimum percentage (e.g., 10%) of maximum amplitude. Subsequently, a plot of the largest continuous flow that has a strength that is greater than the minimum, i.e., a main flow plot, is generated. An example of this main flow plot 44 appears in FIG. 2C. Smaller lumps are discarded as spurts or drips. In doing so, a mechanism for comparing one audio file 26' to another with regard to acquired parameters is provided. The duration and time to peak flow starts at the beginning of the main flow as described above. Integration of other metrics of the main flow also provides a means of comparing one urination event to others;

(e) by use of the main flow plot of the above-mentioned item (d), an analysis is performed in order to generate a set of numerical values that correspond to the strength and duration of urination. These values may be used to compare numerically two or more urination events. An example of such a set of values is shown in an analysis window 46 that appears in FIG. 2D. Values include, but are not limited to, the following:

1. MAXIMUM FLOW—maximum flow measured in arbitrary units recorded in the course of a single urination event;
2. TIME TO MAXIMUM FLOW—a measure of the time from the beginning of the main flow until the maximum amplitude is reached;
3. VOIDING TIME—a measure of the time duration of the main flow, also known as FLOW TIME or DURATION; and
4. AVERAGE FLOW—the arithmetic mean of the main flow in arbitrary units. The average is used for comparing two or more audio files 26'.

and (f) writing the above-mentioned plots and analysis to database 32 of computer 28.

Figure 2A:
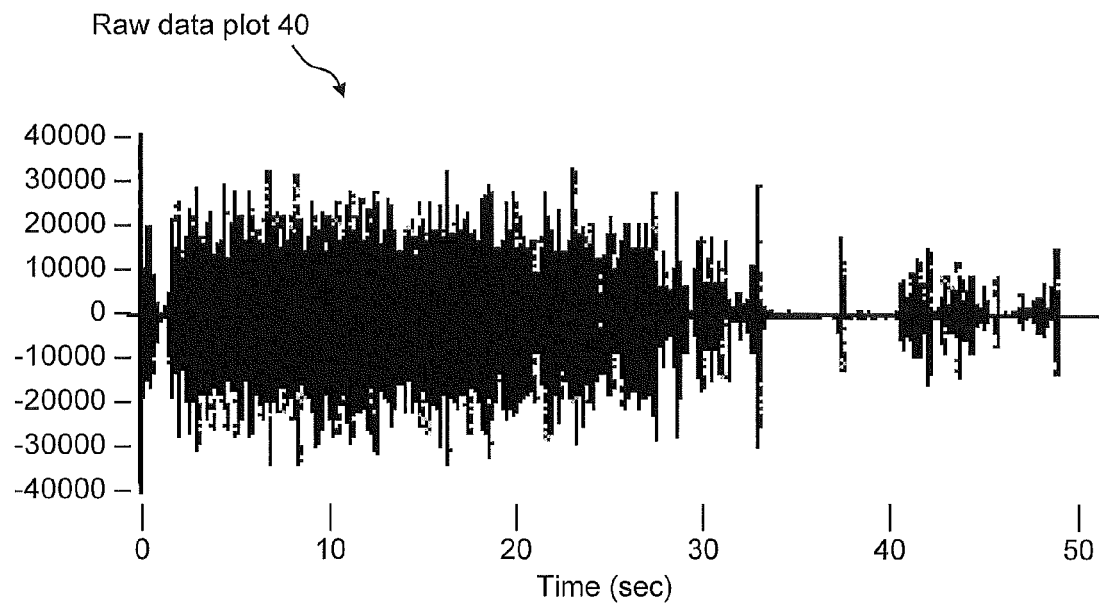
FIG. 2A illustrates a plot of the raw data of an audio file that is generated by recording of a sound energy using measurement system of FIG. 1.

As mentioned, FIG. 2A illustrates a raw data plot 40, which is the raw data from a selected one of audio files 26' that is generated by LUTS assessment system 20 of FIG. 1. More specifically, raw data plot 40 is a plot of audio signal amplitude vs. time of the selected audio file 26' in its entirety, which, again, is the digital representation of the sound of a stream of urine striking the water in a toilet or other receptacle during a urination event.

Figure 2B:
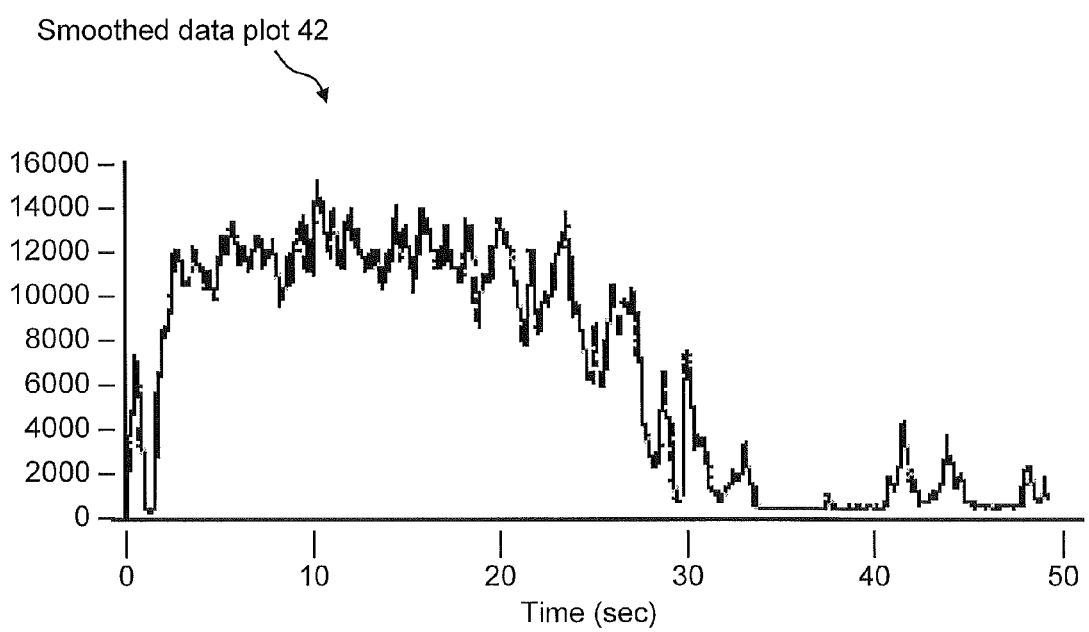
FIG. 2B illustrates an upper envelope of the smoothed data of the raw data plot of FIG. 2A.

FIG. 2B illustrates smoothed data plot 42 of raw data plot 40 of FIG. 2A. More specifically, smoothed data plot 42 is an envelope that is smoothed by a median filter, for example, the maximum positive amplitude per 100 data points of raw data plot 40 of FIG. 2A. In doing so, smoothed data plot 42 shows an outline of the flow of the entire urination event. The present invention encompasses the use of any data smoothing algorithms that produce a result suitable for intended use, as known to those skilled in the art.

Figures 2C, 2D:
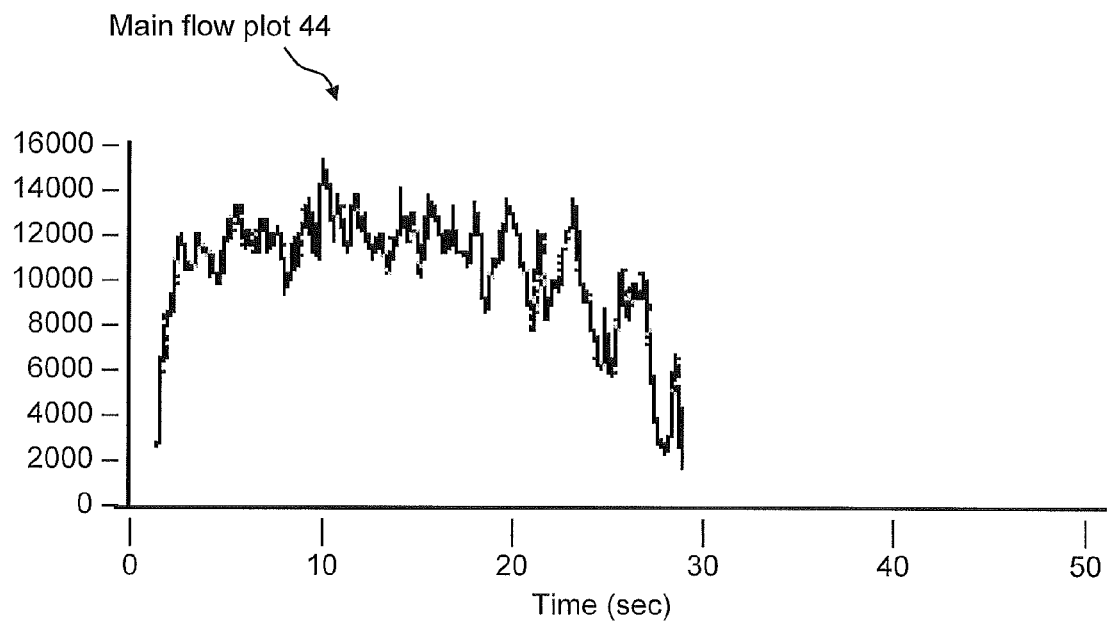
FIG. 2C illustrates a plot of a main flow, which is a subset of the smoothed data of FIG. 2B.
FIG. 2D illustrates an analysis window of the LUTS assessment system of FIG. 1.

FIG. 2C illustrates main flow plot 44, which is a selected portion of smoothed data plot 42 of FIG. 2B. More specifically, main flow plot 44 is a plot of the largest continuous flow that has a strength that is greater than the minimum. Smaller lumps that are present in smoothed data plot 42 that represent spurts or drips are discarded in arriving at main flow plot 44. For example, main flow plot 44 is the result of discarding the smaller leading and trailing lumps of smoothed data plot 42 of FIG. 2B.

FIG. 2D illustrates an analysis window 46 of LUTS assessment system 20 of FIG. 1, which is the result of sound analysis software 30 performing an analysis in order to generate a set of values that correspond to the strength and duration of urination. In the example of analysis window 46, values corresponding to MAXIMUM FLOW, TIME TO MAXIMUM FLOW, AVERAGE FLOW, and DURATION are shown. These values are used in order to compare numerically two or more urination events. More details of the operation and use of LUTS assessment system 20 are provided below in connection with the discussion of FIG. 3.

LUTS information, such as urgency, urge incontinence, nocturia and frequency, may also be captured and, optionally, displayed by LUTS assessment system 20. See, for example, the INTERMICTURITION INTERVAL and URGENCY fields in analysis menu 46 for an example of the manner in which LUTS information may be displayed. As discussed more below, by providing LUTS information in connection with information regarding strength and duration of a urination event, a substantially more robust assessment of lower urinary tract function and bladder overactivity may be determined. LUTS information may be provided via sound-capture device 24. For example, immediately following capture of the sound of micturition by device 24, LUTS information such as urgency of micturition, may be provided.

Optionally, as shown in FIG. 1, LUTS assessment system 20 may include LUTS information capture device 47 to obtain LUTS information and provide it to LUTS files 48 in database 32 in computer 28. LUTS information capture device 47 may have one of a variety of different forms, including without limitation, a paper diary, an electronic diary, an analog or digital recorder, a website with fields for receiving LUTS information, checklists and/or other media for receiving LUTS information, a telephone, alone or in combination with a call center with a live person who accepts LUTS information from a user or an interactive voice response (IVR) system that obtains LUTS information from a user through appropriate prompts and/or queries, and/or via a keyboard, mouse or other data input device. In certain cases, it may be desirable to combine one or more of such LUTS capture approaches in creating LUTS information capture device 47. LUTS information is often provided by a user, but in some cases a family member, healthcare professional or other person may provide, or assist a user in providing, LUTS information.

Discussing LUTS information in somewhat greater detail, one form of LUTS information that may be obtained via sound-capture device 24 or LUTS information capture device 47 is intermicturition interval, i.e., urination frequency. Intermicturition interval, also referred to as just "interval", is a measure of the time elapsed between the current and the most recent past micturition event. A user may measure intermicturition interval, and then provide such information, e.g., via LUTS information capture device 47, to LUTS file 48. Alternatively, or additionally, LUTS assessment system 20 may include LUTS assessment software 49 which, among other functions, may record the time at which first and second urination events occur and then calculate the intermicturition interval based on differences in time at which the urination events occur. Other automated techniques for determining intermicturition interval are also encompassed by the invention, e.g., using a timer that counts down from one micturition to the next. Regardless of how determined, intermicturition interval information may, if desired, be stored in LUTS files 48.

Another form of LUTS information that may be obtained via sound-capture device 24 or LUTS information capture device 47 relates to the subjective urgency of the urination event as perceived by the patient. This urgency information may, for example, be obtained using a five-point urgency scale. For example, a value of "1" could indicate "I felt no need to empty my bladder but did so for other reasons;" a value of "2" could indicate "I could postpone voiding as necessary without fear of wetting myself;" a value of "3" could indicate "I could postpone voiding for a short time without fear of wetting myself;" a value of "4" could indicate "I could not postpone voiding but had to rush to the toilet in order to not wet myself;" and "5" could indicate "I leaked before arriving at the toilet."

The results produced by sound analysis software 30 are managed and accessed through management software 49. This can include providing a graphical user interface via computer 28, or transmission of analysis results, for example by email or voicemail (not shown), to the patient or physician. In addition, management software 49 can obtain sound data from sound capture device 24, make the analysis of such data using sound analysis software 30, store the data in database 32, and manage all processes. In addition, management software 49 can obtain LUTS data from LUTS information capture device 47, and analogously manage the storage, analysis, access, and presentation or communication of such data.

Figure 3:
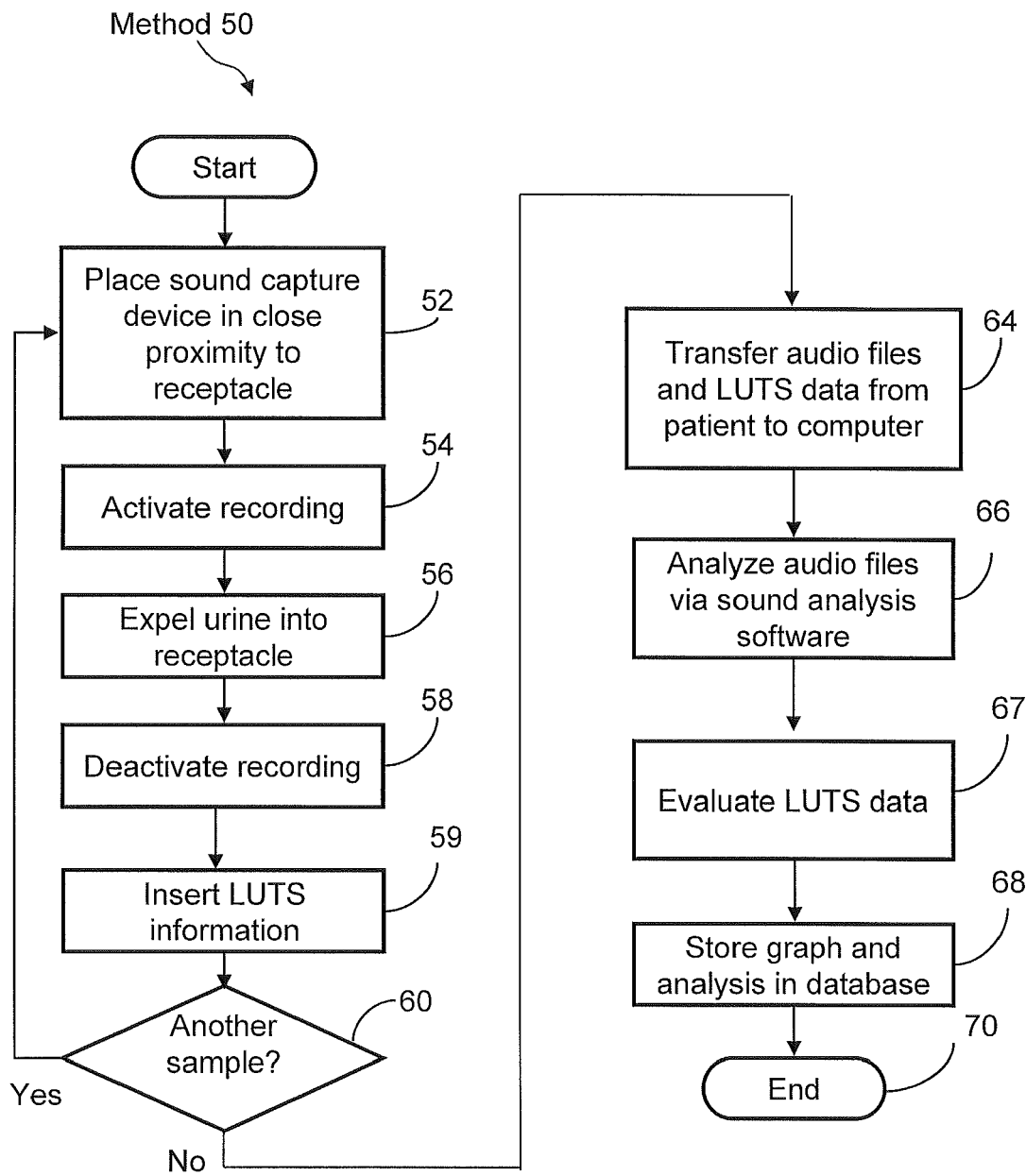
FIG. 3 illustrates a method of assessing urinary flow via sound analysis by use of the LUTS assessment system of FIG. 1, in accordance with a first embodiment of the disclosure.

FIG. 3 illustrates a method 50 of assessing lower urinary tract function via use of LUTS assessment system 20 of FIG. 1, in accordance with one embodiment of the disclosure. At step 52, a user positions sound-capture device 24 in close proximity to the receptacle (not shown) into which he/she wishes to urinate. At step 54, the user activates digital recording device 22, or, when the sound-capture device is connected directly to, or is part of, computer 28, initiates sound capture and recording in the computer. At step 56, the user urinates into the receptacle. In doing so, digital recording device 22, or computer 28 when sound-capture device 24 is connected directly to the computer, captures the sound of the urine stream. At step 58, the user deactivates recording of the urination stream and removes sound-capture device 24, and recording device 22 when used, from the receptacle area.

At step 59, the user may optionally provide subjective information regarding LUTS with respect to the recorded urination event using LUTS information capture device 47 or directly to computer 28 using sound-capture device 24. For example, if the LUTS information of interest is urgency on the five-point urgency scale, step 59 will involve providing a number from 1 through 5 which represents the patient's sense of urgency. This LUTS information is associated with a given user via an appropriate tag, address, ID or other technique. The LUTS information is typically provided immediately before or after the urination event, e.g., within 1 second to 5 minutes before or after urination, although in some cases it may be desirable to provide LUTS information a longer period of time before or after the urination event. LUTS information becomes less reliable as the time between urination and provision of LUTS information increases, although in some cases it may be desirable to not provide LUTS information immediately before or after urination.

At step 60, a determination is made regarding whether or not another sample is to be received. If so, then the process returns to step 52. If not, the process continues to step 64.

At step 64, the user transfers one or more audio files 26 and LUTS information to computer 28 via a USB connection, wireless connection, a memory card, or any other suitable means. In doing so, the one or more audio files 26 are stored upon database 32 of computer 28 as respective audio files 26' and LUTS files 48 along with a tag for each that indicates the patient to which it is associated and/or any other pertinent information. When sound-capture device 24 is connected directly to computer 28, step 64 is not typically performed.

At step 66, sound analysis software 30 reads in each audio file 26' and performs an analysis thereon in order to determine the strength and duration of each urination event, such as described above in connection with FIGS. 1, 2A, 2B, 2C, and 2D. In doing so, a set of graphs, such as raw data plot 40 of FIG. 2A, smoothed data plot 42 of FIG. 2B, and main flow plot 44 of FIG. 2C, along with a set of numerical values, such as shown in analysis window 46 of FIG. 2D, are generated for each urination event. Again, example values that are displayed in analysis window 46 may include, but are not limited to, MAXIMUM FLOW, TIME TO MAXIMUM FLOW, AVERAGE FLOW, and DURATION, as described above in connection with FIGS. 1, 2A, 2B, 2C, and 2D.

LUTS information obtained at step 64 is analyzed at step 67. For example, LUTS information may be used at step 67 to determine intermicturition intervals. In one implementation, a time stamp may be associated with each micturition, and a determination of the difference in time between successive micturitions is performed to establish the intermicturition interval. In another implementation, the user records the time between successive micturitions, determines the time interval between such micturitions and provides the time interval as part of the LUTS information. LUTS information may be analyzed in other ways as well at step 67. For example, if the LUTS information includes urgency data with respect to the micturition, such data may be analyzed over a selected time period to determine the average, median and other attributes of the urgency information.

At step 68, the graphs and values of step 66 are stored in database 32 as corresponding results files 34 for each urination event. Also at step 68, the results of the analysis performed at step 67 may be stored in LUTS file 48. This information may be used for the assessment of bladder overactivity, lower urinary tract symptoms, and as a tool in performing diagnosis of the medical conditions responsible for bladder overactivity or other lower urinary tract disorders. In this regard, a healthcare professional will review the analyzed sound and LUTS information (in some cases LUTS information may be presented without analysis) using his or her background medical knowledge in connection with determining whether bladder overactivity or lower urinary tract symptoms exist, or in the case of more highly trained medical personnel, including doctors, in connection with diagnosing the possible existence of underlying diseases. Method 50 may end at step 70 or may return to, for example, either step 52 or step 54.

A portfolio of audio files will result with repetition of method 50, as well as resulting data from audio file analysis. This information, alone or in conjunction with urgency data for each urination event such as the corresponding five-point urgency scale may be summarized in graphical or tabular formats. This summary provides a means to compare and contrast different urination events, identify trends, and act as a diagnostic tool to provide decision support in evaluating efficacy of treatment plans, when reviewed by appropriate personnel. For example, referring to FIG. 2D, analysis menu 46 may be used to depict selected information regarding a urination event.

Figure 4:
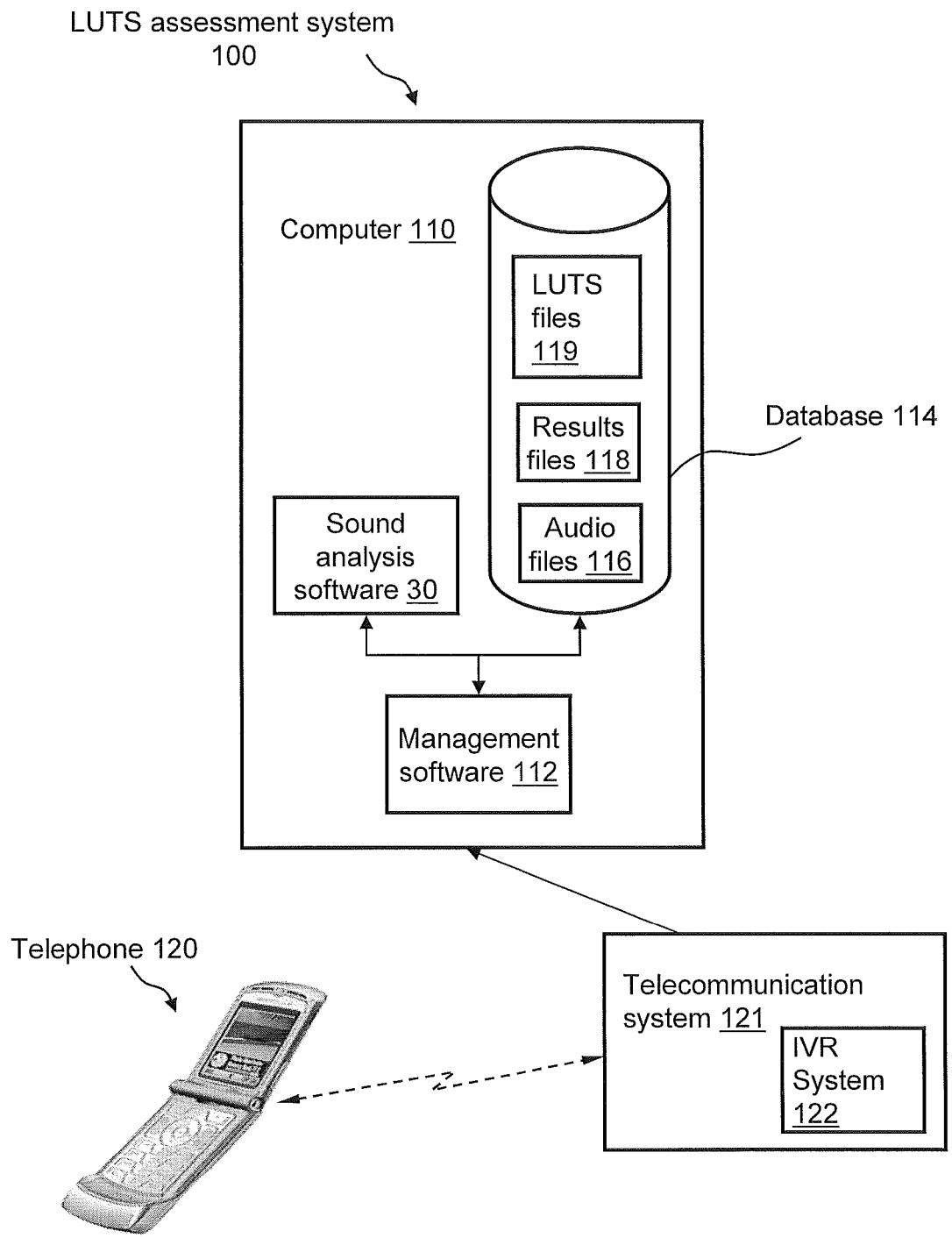
FIG. 4 illustrates a functional block diagram of a LUTS assessment system, in accordance with a second embodiment of the disclosure.

FIG. 4 illustrates a functional block diagram of an LUTS assessment system 100, in accordance with a second embodiment of the disclosure. LUTS assessment system 100 provides mechanisms for measuring urinary flow rate by capturing over the telephone the sound of a patient urinating into a receptacle and, subsequently, performing an analysis thereof in an automated fashion. LUTS assessment system 100 includes a computer 110 that comprises management software 112 and a database 114 upon which is stored a set of audio files 116, LUTS files 119 and a set of results files 118. Computer 110 may be identical to computer 28, as described above, or may be any other type of computer suitable for performing the functions described below. Also residing on computer 110 is sound analysis software 30, as described above in connection with FIGS. 1, 2A, 2B, 2C, 2D and 3. LUTS assessment system 100 further includes a telephone 120 that may be connected to telecommunication system 121 by use of wired, voice-over-IP (VoIP) or cellular infrastructure, as is well known. Computer 110 is connected to telecommunication system 121 so that micturition sounds and LUTS information provided to telephone 120 are delivered to the computer.

In this regard, telecommunication system 121 includes all the infrastructure necessary to result in transmission of sound from telephone 120 to computer 110. Telecommunication system 121 may include, for example, any private or commercially available cellular, landline, VoIP or other telephone service provider. Example telephone service providers include, but are not limited to Vonage (Montreal, Quebec), Verizon Wireless (Bedminster, N.J.), Sprint Nextel (Reston, Va.), Time Warner Cable (Stamford, Conn.), and Verizon (New York, N.Y.). Telecommunication system 121 may capture, store and send telephone recordings (e.g., voice mails). In one implementation, telecommunication system 121 may also host an interactive voice response (IVR) system 122. IVR system 122 may provide a telephone menu system as a means for facilitating input of audio files 116, LUTS files 119, and other user-generated responses or data input into the management software 112. For example, IVR system 122 could provide a voice-prompted menu for entering audio data or audio files, as well as a method for entering LUTS data to be associated with a particular urination event. Alternatively, an IVR system may be provided as part of management software 112 in computer 110 or as an additional component in computer 110.

Management software 112 is the software application that manages the overall functions that are related to assessing attributes of a particular urination event, and so is substantially identical to management software 49 in assessment system 20 of FIG. 1. More specifically, management software 112 obtains urination sound data from telecommunications system 121 (e.g., via e-mail attachment, ftp, directly from the IVR system or other means of transferring sound data or files) or from real-time stream of sound from telephone 120, makes the analysis thereof by use of sound analysis software 30, stores the results in the database 114, and manages all of the foregoing.

Additionally, management software 112 may receive and store associated LUTS information and other patient data that is entered by a user or that enters through telecommunications system 121, as might be entered through a IVR system. When data for consecutive urination events are captured in the results files 118, then urination frequency data can be generated by, and made available through, management software 112. If desired, unrecorded urination events may also be inserted and used by management software 112 in calculating urination frequency. Calculation of the time interval between urination events generates frequency data that can be stored in result files 118 within database 114.

Management software 112 may also be employed to perform other analysis of LUTS information, such as incidence of nocturia over a selected time period and average urgency, e.g., using the five-point scale, associated with urination events over a selected period of time. Such data is diagnostically valuable in assessing lower urinary tract function generally, and more specifically the existence of bladder overactivity and the presence of lower urinary tract symptoms. Management software 112 may also be designed and implemented to develop a graphical depiction of the results of the sound analysis of urination events, selected LUTS information and the results of analysis of the LUTS information, for display in a user interface or in a document. Optionally, the results of the urination sound analysis and LUTS information analysis may be communicated back to the user by email, ftp or other means of transferring digital files, or made available on a web site in a user interface. Telephone 120 may be any commercially available (or specifically constructed) telephone or cellular telephone.

Database 114 may be created and maintained by any suitable database management software, such as the above-mentioned Oracle database software, that stores relationships between patients and their associated audio files 116, LUTS files 119, and results files 118. Audio files 116 are audio files of the sound of corresponding respective urination events that are received at telecommunications system 121 via telephone 120. Audio files 116 may have any suitable audio file format, such as WAV format or MP3 format. Each audio file 116 is typically associated with a particular patient and may, if desired, carry a timestamp. Results files 118 are data files that contain the results of the digital analysis of respective audio files 116. This analysis is performed by sound analysis software 119, for example, as described above in connection with software 30 and FIGS. 1, 2A, 2B, 2C, 2D and 3.

Figure 5:
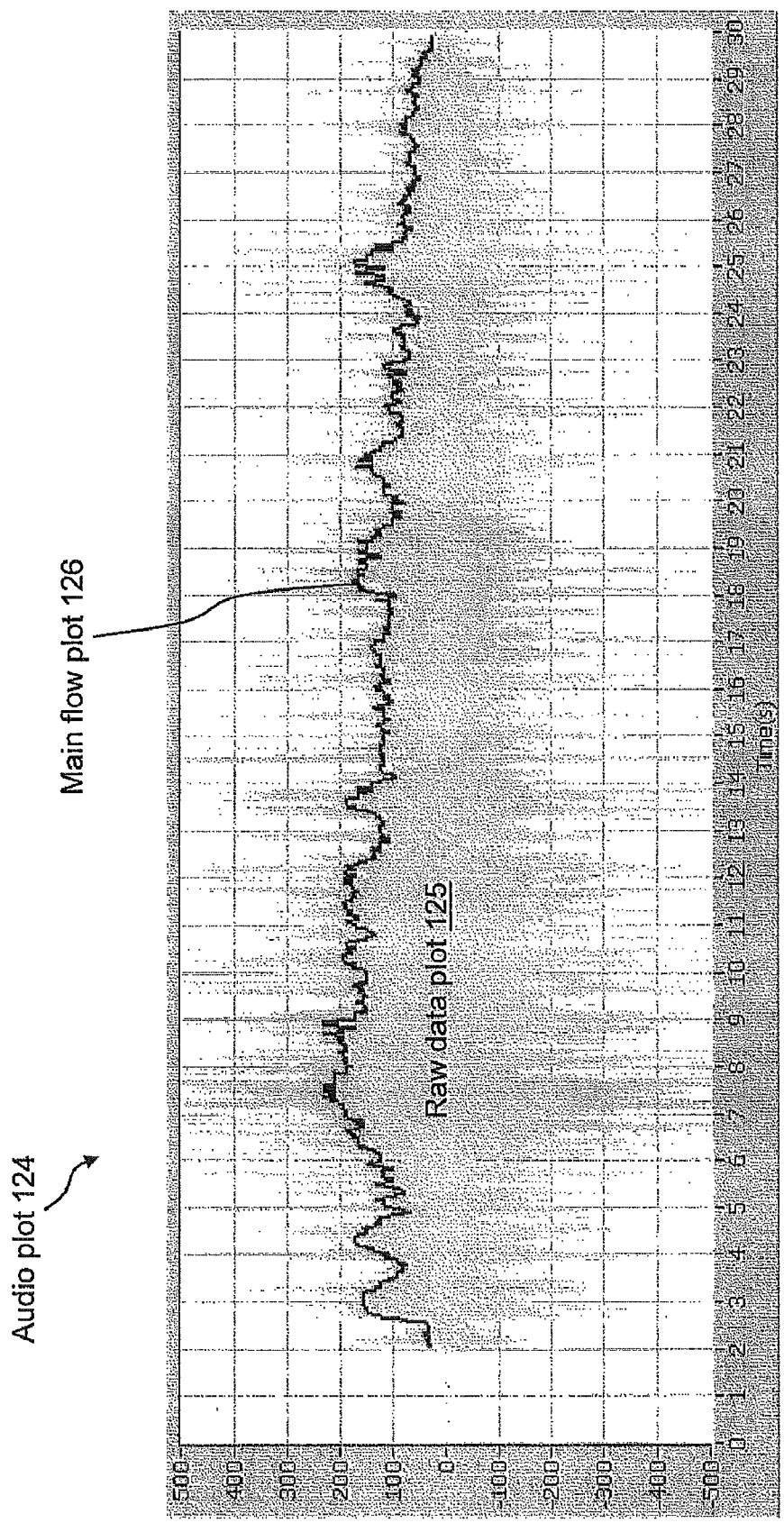
FIG. 5 illustrates a plot showing both the raw data and the main flow as derived from an audio file that is generated by use of the LUTS assessment system of FIG. 4.

FIG. 5 illustrates a combined audio plot 124 derived from an audio file 116 that may be generated by use of LUTS assessment system 100 of FIG. 4. Audio plot 124 is a combination of a raw data plot 125 upon which is overlaid a main flow plot 126. More specifically, raw data plot 125 is a plot of audio signal amplitude vs. time of a selected audio file 116 in its entirety, which is the digital representation of the sound of a stream of urine during a urination event, such as described above with respect to raw data plot 40 of FIG. 2A. Main flow plot 126 is a selected portion of raw data plot 125. More specifically, main flow plot 126 is a plot of the largest continuous flow having a strength greater than some predetermined minimum. Smaller lumps that are present in raw data plot 125 that represent spurts or drips are discarded generally in the manner described with respect to main flow plot 44 of FIG. 2C. More details of the operation and use of LUTS assessment system 100 are presented below in connection with FIG. 6.

Figure 6:
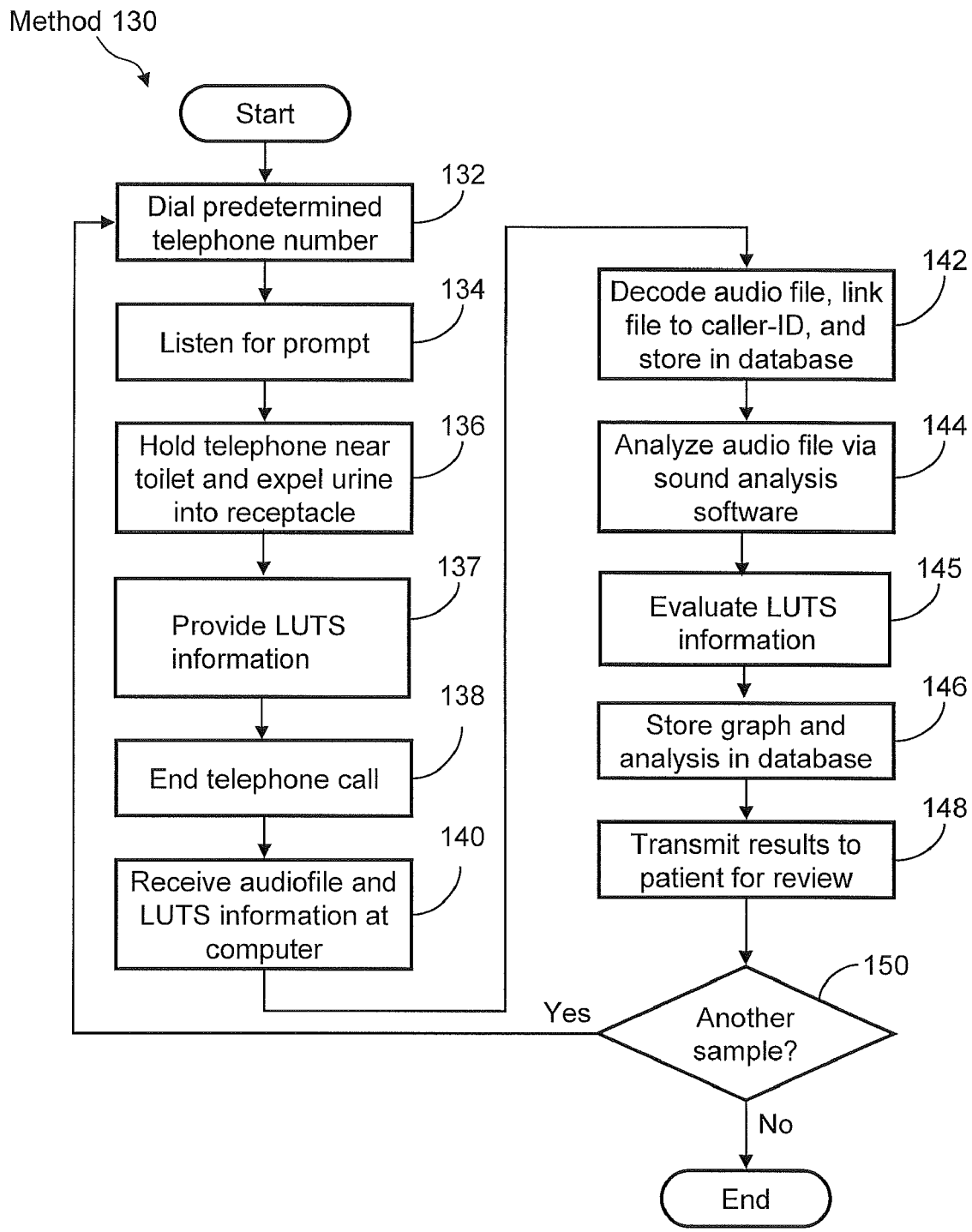
FIG. 6 illustrates a method of automatically assessing urinary flow rate via sound analysis by use of the LUTS assessment system of FIG. 4, in accordance with a second embodiment of the disclosure.

FIG. 6 illustrates a method 130 of assessing lower urinary tract function using sound analysis of micturition and associated LUTS information with LUTS assessment system 100 of FIG. 4, in accordance with a second embodiment of the disclosure. At step 132, a user who wishes to have his/her lower urinary tract function analyzed or wishes to record a test dials a predetermined telephone number by use of his/her telephone 120. In doing so, the user's telephone 120 is connected via a telecommunications system 121 with LUTS assessment system 100. The user may also be connected to a voicemail or Interactive Voice Response (IVR) system 122 which stores the sounds of urination for later processing by sound analysis software 30, as discussed above. The phone number may be, for example, a toll free telephone number that is established by the administrator of LUTS assessment system 100.

At step 134, having dialed the predetermined telephone number at step 132, the user listens on his/her telephone 120 for a prompt to begin urinating into his/her toilet or other receptacle. The prompt may be a beep, prerecorded voice, or any audible prompt. At step 136, a user positions his/her telephone 120 near to the receptacle (not shown) into which he/she wishes to urinate. Subsequently, the user urinates into the receptacle. In doing so, the sound is transmitted via telephone 120 through telecommunication system 121 to computer 110.

Next, at step 137, the user enters selected LUTS information, such as the score on the five-point urgency scale, using the telephone keypad or by voice. In some cases, it may be desirable to obtain LUTS information immediately prior to the urination event, and in yet other cases, it may be desirable to provide LUTS information in a prior or subsequent call. As noted above, while the most reliable LUTS information is typically obtained immediately after the urination event, the invention is not so limited. At step 138, upon completion of the urination event and provision of LUTS information, the telephone call is ended.

At step 140, upon completion of the telephone call, the sounds of urination and LUTS information is received by computer 110. An audio file 116 of the sounds of urination may then be generated at computer 110 and stored in database 114. Audio file 116 is the digital representation of the sound of the urine stream during micturition. Also at step 140, LUTS information provided is stored in a LUTS file 119 in database 114. At step 142, management software 112 of computer 110 links the given audio file 116 and LUTS file 119 to an ID associated with the user. The precise sequence in which a given audio file 116 and LUTS file 119 are stored in database 114 will vary with implementation selected by a user of LUTS assessment system 100, although in many cases it will be desirable to provide information in audio file 116 and in LUTS file 119 with unique identification information and a timestamp.

At step 144, sound analysis software 30 reads in the given audio file 116 and performs an analysis thereon in order to determine the strength and duration of the urination event, such as described with reference to FIGS. 1 through 5. In doing so, a set of graphs, such as shown in audio plot 124 of FIG. 5 (e.g., raw data plot 125 and main flow plot 126), along with a set of values, such as shown in analysis window 46 of FIG. 2D, are generated for the urination event. Example values include, but are not limited to, MAXIMUM FLOW, TIME TO MAXIMUM FLOW, AVERAGE FLOW, and DURATION, as described with respect to FIGS. 1, 2A, 2B, 2C and 2D.

At step 145, management software 112 reads the associated LUTS file 119 in order to tabulate, evaluate (e.g., to determine an average urgency score over a selected time period) and summarize LUTS information, such as urgency, urge incontinence, nocturia and frequency.

At step 146, the graphs and values of the urination event determined at step 144 and any LUTS information evaluated at step 145 are stored in database 114 as a corresponding results file 118 for the given urination event. Also at this step, the information in results file 118 may be incorporated by management software 112 in a user interface such as a web page, document or any other suitable medium. As described above, some or all of the information in results file 118 may be used for the assessment of bladder overactivity, lower urinary tract function and for use in diagnosing underlying diseases.

At step 148, the graphs and values of urination and LUTS information stored at step 146, which include the results of the analysis that is performed in step 144, may be transmitted to the patient's doctors and/or the patient for review. The transmission may occur, for example, via email, fax, picture messages to cell phones, voicemail or other ways, under the control of management software 112 of computer 110. Also a web site link may be provided into which the patient may log in and access his/her results. At decision step 150, the user decides whether he/she wishes to supply another sample, i.e., another audio file 116 and associated LUTS information. If yes, method 130 returns to step 132. If no, method 130 may end.

Figure 7:
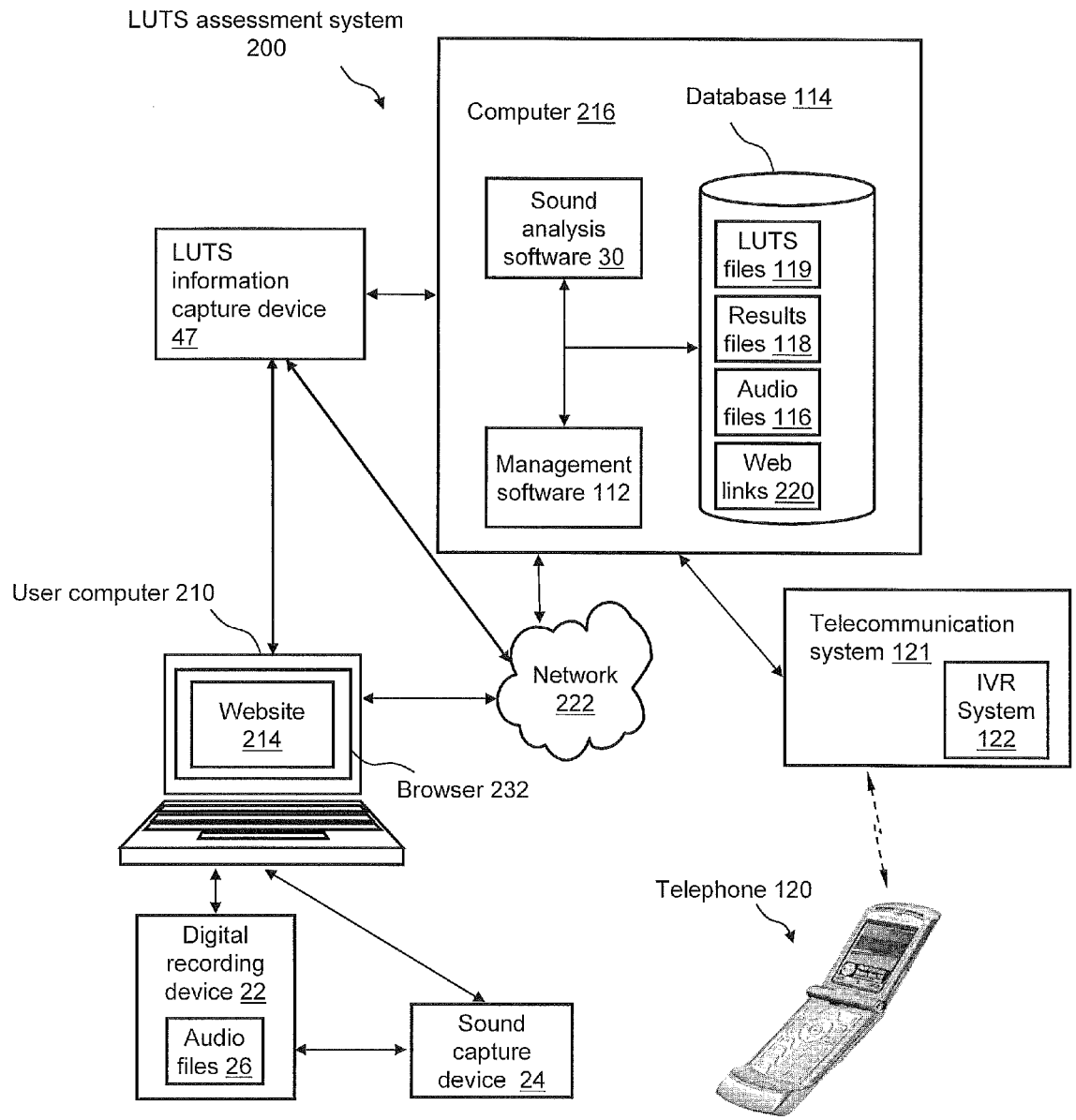
FIG. 7 illustrates a functional block diagram of a LUTS assessment system, in accordance with a third embodiment of the disclosure.

FIG. 7 illustrates a functional block diagram of a LUTS assessment system 200, in accordance with a third embodiment of the disclosure. This embodiment provides multiple flexible means for inputting both sound data and LUTS data from remote or local locations, as well as accessing resulting analysis files. LUTS assessment system 200 includes a user computer 210 that is in communication with digital recording device 22 that contains audio files 26 and that is connected to sound-capture device 24. Digital recording device 22, sound-capture device 24, and audio files 26 as described above in connection with LUTS assessment system 20 of FIG. 1. As also discussed above, if user computer 210 includes sound capture and recording capabilities, sound-capture device 24 may be connected directly to user computer 210, or may be an integral part of the computer. Additionally, user computer 210 includes a browser 232 by which a website 214 is displayed to the user of user computer 210.

LUTS assessment system 200 further includes a computer 216 having sound analysis software 30, management software 112, and database 114, which are described above in with connection LUTS assessment system 100 of FIG. 4. Database 114 includes audio files 116, results files 118, and LUTS files 119, which are also described above in connection with LUTS assessment system 100 of FIG. 4, and a collection of web links 220. In addition to performing the functions described above with respect to LUTS assessment system 100, management software 112 also supports and manages the website links stored in web links 220. As described more below, user computer 210 may be used in connection with one or more of the following operations: (i) providing urination sounds to computer 216, (ii) providing LUTS information to computer 216, and (iii) receiving information regarding attributes of urination and regarding LUTS from computer 216.

LUTS assessment system 200 may optionally include telephone 120 and telecommunications system 121, which are likewise described above in connection with LUTS assessment system 100 of FIG. 4. Since telecommunication system 121 and/or computer 216 may include an interactive voice response (IVR) telephone answering system, IVR system 122, that can provide a user with prompts or other directions for inputting LUTS information into database 114, LUTS assessment system 200 provides a second approach for entering the sound of a urination event and/or LUTS information to computer 216 (user computer 210 being the first approach, as discussed more below).

A communication link may be provided between user computer 210 and computer 216 through the use of a network 222. The latter may be any suitable wired or wireless network, such as a local area network (LAN), a wide area network (WAN), or the Internet.

As discussed above with respect to computer 28, user computer 210 and computer 216 may be any standard computer or computing resource, such as a handheld, laptop, desktop, or networked computer, that utilizes any suitable operating system, such as Microsoft Windows® 2000, Windows XP, Unix, Linux, or Macintosh, that is capable of executing commercially available software applications or custom software applications, such as, in the case of computer 216, sound analysis software 119 or management software 112.

Browser 232 of user computer 210 may be any suitable Internet browser application, such as, but not limited to, Windows® Internet Explorer or Firefox. Website 214 permits a user to access management software 112 of computer 216 via network 222. More specifically, management software 112 allows a user to access, via his/her user computer 210, web links 220 of database 114 that are associated with website 214. Website 214 provides a graphical user interface (GUI) by which the user may access management software 112, database 114, and sound analysis software 30. In particular, under the control of management software 112, a user may log in to the web-based application. The function of management software 112 as implemented in computer 216 is substantially identical to that of management software 112 of LUTS assessment system 100 of FIG. 4, with one exception. As implemented in computer 216, management software 112 provides the additional function of managing web-based applications that allow a patient, doctor, or other authorized party to log in and view the results of the sound analysis of one or more urination events that is performed by sound analysis software 30 and LUTS information in LUTS files 119, whether in raw form or after being analyzed in some respect.

In doing so, the strength and duration of one or more urination events, such as described with connection to FIGS. 1 through 6, are displayed to the user via website 214 in the display of user computer 210. More specifically, and as discussed further in connection with FIGS. 8A and 8B below, a set of graphs, along with a set of numerical values for attributes of micturition, such as, but not limited to, FLOW TIME, AVERAGE FLOW, MAXIMUM FLOW, TIME TO MAXIMUM FLOW and INTERMICTURITION INTERVAL are presented to the user via website 214. Further, degree of urgency measured using the five-point urgency scale and other LUTS information, not shown, may also be presented to the user via website 214.

Figure 8A:
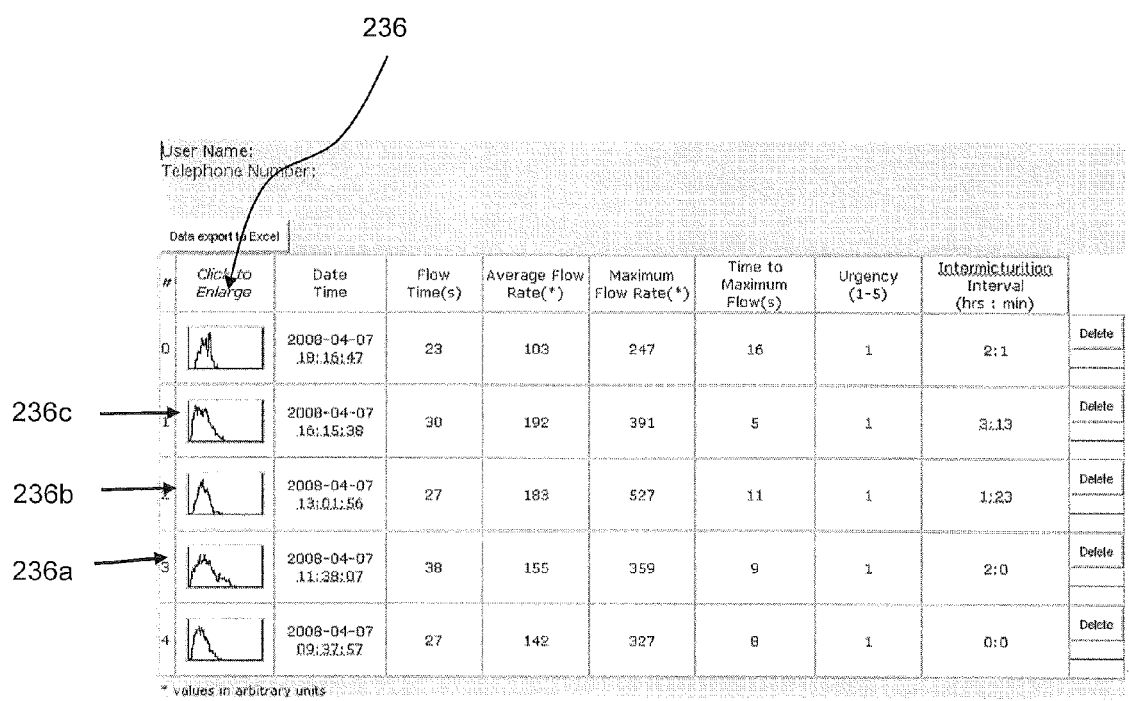
FIG. 8A illustrates a user interface that is provided by use of the LUTS assessment system of FIG. 7.

FIG. 8A illustrates user interface 234, which is one example of an interface that may be displayed in website 214. In user interface 234, the analysis of multiple urination events from the same individual is displayed to the user in browser 232 of his/her user computer 210. Displayed as a numerical value for each of the urination events is a FLOW TIME, AVERAGE FLOW, MAXIMUM FLOW, TIME TO MAXIMUM FLOW, and INTERMICTURITION INTERVAL (i.e., intermicturition interval as measured with respect to the immediately prior micturition). Also displayed for each of the urination events is a collection of "thumbnail" results plots 236, e.g., thumbnail results plots 236a, 236 and 236c. In one embodiment of website 214, by clicking on a selected one of thumbnail results plots 236, e.g., one of plots 236a-c, the selected results plot is enlarged, as shown in more detail in FIG. 8B.

Figure 8B:
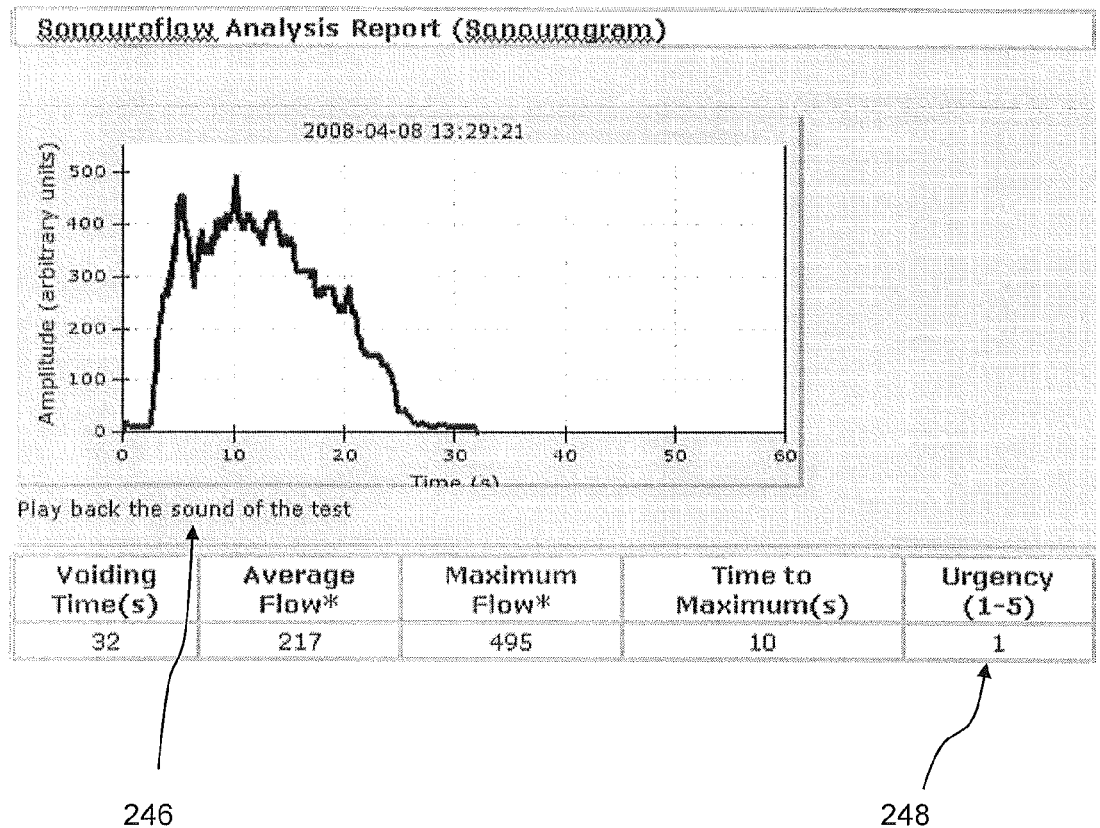
FIG. 8B illustrates an example results plot user interface that is provided by use of the LUTS assessment system of FIG. 7.

FIG. 8B illustrates an example results plot 236 on a user interface 244 that may be displayed in website 214 of LUTS assessment system 200 of FIG. 7. More specifically, results plot 236 of website 214 is a graphical representation of a particular urination event and is combined with tabulated measures of the event analysis, such as "Voiding Time", and may include the ability to access and replay the sound recording 246 of the urination event. Other lower urinary tract symptom data input by the user, such as the event's value on the five-point urgency scale is also displayed. While user interfaces 234 and 244 are suitable for display in website 214, they may also be used in non-website environments, e.g., in connection with equipment dedicated to analysis of micturition sound and LUTS or conventional general-purpose computing devices such as computers 28, 110 and 216 or phone screen display.

Referring again to FIGS. 7, 8A, and 8B, the operation of LUTS assessment system 200 is as follows. An audio file of a urination event is captured by use of digital recording device 22 and sound-capture device 24, with user computer 210 (assuming it has sound-capture functionality) or by use of telephone 120. In the case of user computer 210 or digital recording device 22 and sound-capture device 24, the urination event is stored as an audio file 26. When audio file 26 is captured in digital recording device 22, the file is then transferred to user computer 210 (of course, the sound recording is already in an audio file 26 in user computer 210 when the urination sound is captured directly by the user computer). Then, a user may email (by any conventional email application) the audio file 26 to computer 216 via network 222. Alternatively, website 214 may be designed to transfer audio file 26 to computer 216. The user's audio file 26 is saved in database 114 as, for example, an audio file 116. When a patient uses telephone 120, the sound of a urination event is transferred to computer 216 via telecommunication system 121, as described in connection with LUTS assessment system 100 of FIG. 4. Again, the user's audio file is saved in database 114 as, for example, an audio file 116. In either case, stored along with audio file 116 may be an identification mechanism (e.g., a telephone number) for linking the file to its source (i.e., to a specific patient) and a timestamp. Having saved one or more audio files 116 to database 114 of computer 216, sound analysis software 30 executes in order to generate values, for example, for FLOW TIME, MAXIMUM FLOW, TIME TO MAXIMUM FLOW, AVERAGE FLOW, and INTERMICTURITION INTERVAL, for incorporation with other LUTS data, for example, the scores on the five-point urgency scale and creation of the plots of the urination event, such as results plots 236a, 236b, and 236c, as shown in user interface 234 of FIG. 8A.

As discussed above, LUTS information such as the urgency on the five-point urgency scale, may be input by various known means, including telephone 120 and LUTS information capture device 47. In regard to the latter, LUTS information capture device 47 may be connected directly to computer 216, via network 222 to computer 216 or via user computer 210 to computer 216.

In summary, a lower urinary tract symptoms (LUTS) assessment system made in accordance with the present disclosure, such as LUTS assessment system 20 of FIG. 1, LUTS assessment system 100 of FIG. 4, and LUTS assessment system 200 of FIG. 7, provide mechanisms for assessing lower urinary tract function using sound analysis software 30 and other data management software 49 and 112 with data originating from remote or local locations. LUTS assessment systems 20, 100 and 200 are designed for easy use in a patient's home or work, which eliminates the negative effects and stressfulness of the test environment of a clinic or a hospital and, provides more reliable test results. LUTS assessment systems 20, 100 and 200 may be used for initial screening and follow-up with treatment of persons in all age groups, including pediatric and adolescent patients. Additionally, the use of LUTS assessment systems 20, 100 and 200 allows the micturition process to be studied, which can lead to a better understanding of the development of several types of abnormal voiding habits during early childhood and puberty that later lead to specific voiding dysfunctions. Additionally, the use of these LUTS assessment systems provides patients an easy and quick way to assess their own lower urinary tract function and treatment effects. This is beneficial for treatments such as biofeedback for children with dysfunctional voiding. Clinicians obtain more accurate information and are better able to monitor the dynamics of the disease and the progress of therapy management overall. Furthermore, the use of a LUTS assessment system of the type described in the present disclosure may allow mass preventive examinations, more precisely select patient population seeking medical help and diminish the contact of medical personnel with urine excrements.

In addition, the use of a LUTS assessment system of the present disclosure, that provides urine flow measurement based on sound transduction and LUTS information may be used in medical research in order to test effects of new drugs that are intended to be employed in the treatment of bladder dysfunctions.

While the present invention may be satisfactorily performed using a toilet to receive the urination, it is not so limited. If desired, urination may occur in other receptacles. Generally speaking, suitable alternative receptacles will tend to reflect rather than absorb the sounds of urination so as to permit the sounds of urination to be readily transmitted and captured by digital recording device 22 or other suitable device.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A method of assessing lower urinary tract function of a person, comprising:
   capturing the sound of a person's micturition into an air-liquid interface with a sound-capture device;
   providing information with respect to one or more lower urinary tract symptoms associated with the micturition using the sound-capture device;
   analyzing the sound of micturition to determine at least one of the following attributes of the micturition: strength and duration; and
   analyzing the information with respect to one or more lower urinary tract symptoms together with or without the one or more of said attributes of the micturition for the assessment of lower urinary tract function.

2. A method according to claim 1, wherein the capturing step includes capturing the sound of a person's micturition at a first location and at about the same time providing the sound to a second location that is remote from the first location, the providing step includes providing the information from the first location to the second location, and the analyzing step includes analyzing the sound of micturition at the second location.

3. A method according to claim 1, further including the step of displaying (i) the information and (ii) at least one of the strength and duration attributes, in a user interface.

4. A method according to claim 1, wherein the sound-capture device is a telephone.

5. A method according to claim 1, where in the sound-capture device is microphone not part of a telephone.

6. A method according to claim 2, wherein the sound of micturition and the information is transferred to the second location using a telecommunication network.

7. A method according to claim 1, wherein the providing step includes using an interactive voice response system to assist a user in providing the information.

8. A method according to claim 2, further including analyzing at the second location the information provided over a first period of time to determine frequency of micturition during the first period of time.

9. A method according to claim 1, further including determining frequency of micturition over a first time period based on the time between successive transfers of the sound of micturition during the first time period.

10. A method according to claim 1, wherein the capturing step further includes converting the sound of micturition to a digital file and storing the file in an electronic database.

11. A method according to claim 1, further including determining whether or not the person has bladder overactivity or other lower urinary tract dysfunction based on the information and the sound of micturition.

12. A method according to claim 1, wherein the providing step is performed 1 second to 5 minutes before or after the capturing step.

13. A method according to claim 1, wherein the information includes an identification of the urgency of the micturition.

14. A method according to claim 1, wherein the information includes an indication whether or not the micturition occurred as consequence of nocturia.

15. A method according to claim 1, wherein the information includes an indication whether or not the micturition occurred as urge incontinence.

16. A method according to claim 1, wherein the analyzing step further includes the step of analyzing the sound of micturition to determine at least one of the following: mean flow, maximum flow and interval.

17. A method of assessing lower urinary tract function of a person, comprising:
- transferring the sound of a person's micturition provided to a sound-capturing device at a first location from the first location to a second location remote from the first location, wherein the transferring occurs substantially simultaneously with the micturition via a telecommunications network;
- providing information with respect to one or more lower urinary tract symptoms associated with the micturition to the sound-capturing device at the first location from the first location to the second location via the telecommunications network 1 second to 5 minutes before or after before or after the micturition;
- analyzing the sound of micturition to determine at least one attribute of the micturition; and;
- analyzing the information with respect to one or more lower urinary tract symptoms with or without one or more of the attributes of the micturition for the assessment of lower urinary tract function.

18. A method according to claim 17, further comprising displaying the at least one attribute and at least some of the information with respect to lower urinary tract symptoms in a remote location display.

19. A method according to claim 17, further comprising prompting performance of the transferring and providing steps with a prompt that is perceivable by a human being.

20. A system for assessing lower urinary tract function of a person using urinary flow data and lower urinary tract symptom data from the person, the system comprising:
- a storage medium in which may be stored (i) an audio file including information representing the sound of urination of a person and (ii) lower urinary tract symptom data for the person;
- a device for obtaining and, when connected to a telecommunications network, providing to the storage medium via the telecommunications network, both the sound of urination of a person and lower urinary tract symptom data for the person; and
- a management tool for retrieving and evaluating said audio file and said lower urinary tract symptom data so as to assess lower urinary tract function of the person.

21. A system according to claim 20, wherein said device is a telephone.

22. A system according to claim 21, further comprising an interactive voice response system in communication with said telephone for guiding the person with respect to capturing and providing said sound of urination and said lower urinary tract symptom data to said storage medium.

23. A system according to claim 20, further including a software program stored on a storage medium that analyzes said sound of urination to define at least one of the following: strength and duration, and includes instructions for organizing and displaying at least some of said lower urinary tract symptom data.

* * * * *